(12) United States Patent
Coe et al.

(10) Patent No.: US 6,942,850 B2
(45) Date of Patent: Sep. 13, 2005

(54) AQUEOUS ALCOHOLIC ANTIPERSPIRANT COMPOSITION CONTAINING CALCIUM ENHANCED ANTIPERSPIRANT SALT

(75) Inventors: Craig M. Coe, Sagamore Beach, MA (US); Yan-Fei Shen, Canton, MA (US)

(73) Assignee: The Gillette Company, Boston, MA (US)

( * ) Notice: Subject to any disclaimer, the term of this patent is extended or adjusted under 35 U.S.C. 154(b) by 86 days.

(21) Appl. No.: 10/641,926

(22) Filed: Aug. 15, 2003

(65) Prior Publication Data

US 2005/0036969 A1 Feb. 17, 2005

(51) Int. Cl.[7] .............................. A61K 7/32; A61K 7/34; A61K 7/38; A61K 7/00
(52) U.S. Cl. .............................. 424/65; 424/66; 424/68; 424/400; 424/401
(58) Field of Search .............................. 424/65, 66, 68, 424/400, 401

(56) References Cited

U.S. PATENT DOCUMENTS

| | | | |
|---|---|---|---|
| 3,979,510 A | 9/1976 | Rubino | 424/47 |
| 5,955,065 A | 9/1999 | Thong et al. | 424/68 |
| 5,972,320 A | 10/1999 | Moloney et al. | 424/65 |
| 5,989,531 A | 11/1999 | Schamper et al. | 424/65 |
| 6,042,816 A * | 3/2000 | Shen | 424/65 |
| 6,245,325 B1 | 6/2001 | Shen | 424/65 |
| 6,468,512 B1 | 10/2002 | Carmody | 424/65 |
| 2003/0026773 A1 | 2/2003 | Swaile et al. | 424/65 |
| 2004/0115147 A1 | 6/2004 | Vu et al. | 424/66 |

OTHER PUBLICATIONS

PCT Search Report and Written Opinion from counterpart application PCT/US2004/026083.

* cited by examiner

Primary Examiner—Shelley A. Dodson
(74) Attorney, Agent, or Firm—Stephan Williams

(57) ABSTRACT

Disclosed is a liquid aqueous alcoholic antiperspirant composition comprising, by weight, about 10% to about 60% ethanol, water, and about 8% to about 22% (USP) antiperspirant salt dissolved in the composition, wherein said antiperspirant salt comprises a calcium enhanced aluminum-zirconium chlorohydrate. The composition may optionally include a thickening agent to increase the viscosity of the solution. A more viscous solution is less prone to dripping from the skin or leaking from the dispensing container. Ideally, the composition will provide an absolute sweat reduction significantly higher than currently available antiperspirant products, typically at least 60% sweat reduction or higher.

19 Claims, No Drawings

AQUEOUS ALCOHOLIC ANTIPERSPIRANT COMPOSITION CONTAINING CALCIUM ENHANCED ANTIPERSPIRANT SALT

BACKGROUND OF THE INVENTION

The present invention relates to enhanced efficacy antiperspirant compositions that are aqueous alcoholic solutions.

In U.S. Pat. No. 6,245,325 there is described enhanced efficacy antiperspirant salts that are stable in aqueous solution. These salts include a soluble calcium salt such as calcium chloride and a soluble amino acid such as glycine. Typically, these salts have a Ca:Al+Zr weight ratio of about 1:1 to about 1:28 and an amino acid:Al+Zr weight ratio of about 2:1 to about 1:20. Because these salts retain their enhanced efficacy in aqueous solution, they have an advantage over conventional enhanced efficacy salts that revert to the non-enhanced form in aqueous solution. For the sake of brevity, these salts are hereinafter identified as "CEAZCH" for calcium enhanced aluminum-zirconium chlorohydrate.

It would be highly desirable to produce an antiperspirant composition with significantly improved antiperspirant efficacy over commercially available antiperspirant products. It would be particularly desirable to produce such a composition in a liquid or solution form that can be delivered either through a roll-on applicator or a porous dome applicator.

SUMMARY OF THE INVENTION

The present invention embraces a liquid aqueous alcoholic antiperspirant composition comprising, by weight, about 10% to about 60% ethanol, water, and about 8% to about 22% (USP) antiperspirant salt dissolved in the composition, wherein said antiperspirant salt comprises a calcium enhanced aluminum-zirconium chlorohydrate. The composition may optionally include a thickening agent to increase the viscosity of the solution. A more viscous solution is less prone to dripping from the skin or leaking from the dispensing container. Ideally, the composition will provide an absolute sweat reduction significantly higher than currently available antiperspirant products, typically at least 60% sweat reduction or higher, up to about 70% sweat reduction.

DETAILED DESCRIPTION OF THE INVENTION

The antiperspirant composition of the present invention is in the form of an aqueous alcoholic liquid solution. The composition will generally comprise, by weight, about 10% to about 60%, preferably about 15% to about 55%, more preferably about 18% to about 50%, ethanol. The composition will also include about 8% to about 22% (USP), preferably about 15% to about 20% (USP), antiperspirant salt dissolved in the composition. The antiperspirant salt comprises a calcium enhanced aluminum-zirconium chlorohydrate. The amount of water in the composition will vary depending upon the other components in the composition and the amount of such components. Typically the composition will include about 10% to about 80% water, more typically about 25% to about 70%, most typically about 30% to about 60%. The composition may optionally include a thickening agent to increase the viscosity of the solution, as well as various other components, such as fragrance, to improve its aesthetic properties.

The antiperspirant salts that may be utilized in the compositions of the present invention are calcium enhanced aluminum-zirconium chlorohydrate (CEAZCH) salts. By this term is meant antiperspirant salts as described in U.S. Pat. No. 6,245,325, which is incorporated herein by reference. These salts are aluminum-zirconium chlorohydrates (Al:Zr=2–10; M:Cl=0.9–2.1) that, as 10% solutions, have an HPLC peak 4 to peak 3 area ratio of at least 0.5, preferably at least 0.7, more preferably at least 0.9, with at least 70%, preferably at least 80%, of the aluminum contained in said peaks 3 and 4. These salts include a soluble calcium salt in an amount to provide a Ca:Al+Zr weight ratio of about 1:1 to about 1:28, preferably about 1:2 to about 1:25. They also include a water soluble amino and/or hydroxy acid in an amount to provide an acid:Al+Zr weight ratio of about 2:1 to about 1:20, preferably about 1:1 to about 1:10. Typical calcium salts include calcium chloride, calcium bromide, calcium nitrate, calcium citrate, calcium formate, calcium acetate, calcium gluconate, calcium ascorbate, calcium lactate, calcium glycinate and mixtures thereof. Calcium carbonate, calcium sulfate and calcium hydroxide may also be used because they will dissolve in an aqueous solution of the antiperspirant salt. Typical amino and/or hydroxy substituted lower alkanoic acids include any of the amino acids such as glycine, alanine, valine, leucine, isoleucine, β-alanine, serine, cysteine, β-amino-n-butyric acid, γ-amino-n-butyric acid, etc. and hydroxy acids such as glycolic acid and lactic acid, as well as mixtures of any of these. Glycine is most preferred. At least a portion of the amino acid may be added in its salt form, such as, for example, calcium glycinate.

The calcium enhanced aluminum-zirconium chlorohydrate salts are preferably used as concentrated aqueous solutions, typically containing about 25% to about 38% active (USP). Such compositions will also typically contain about 0.5% to about 2.5% by weight Ca, preferably about 1.0% to about 2.0% by weight Ca, and about 2% to about 6%, preferably about 3% to about 4%, by weight amino acid (or hydroxy acid). Sufficient concentrated aqueous solution is added to the composition of the present invention to provide the desired amount of active (typically 8% to 22% USP) in the final composition. A particularly advantageous antiperspirant salt solution will contain aluminum-zirconium tetrachlorohydrex-gly or aluminum-zirconium octachlorohydrex-gly and calcium chloride (particularly at concentrations of 28–29% USP active, 1.7–1.8% Ca and 3.4–3.5% Gly).

The composition may also include other cosmetic ingredients that are soluble or dispersible therein and that provide desired aesthetic properties, and that preferably do not adversely impact the antiperspirant efficacy of the composition. For example, it may be desired to include polyhydric alcohols (typically with 3 to 9 carbon atoms), such as propylene glycol, dipropylene glycol, tripropylene glycol or sorbitol. If included, the amount of polyhydric alcohol will fall within the range of about 0.5% to about 10% of the composition by weight. It may also be desired to include a surfactant such as C11-15 Pareth-12, PPG-5-Ceteth-20, PEG-40 Hydrogenated Castor Oil, etc. Other optional ingredients may include a fragrance, an encapsulated fragrance, a colorant, a deodorant active agent, an odor-masking agent, an emollient, or a combination of one or more of these.

The foregoing list of materials is by way of example only and is not intended to be a comprehensive list of all potential materials that may be useful in an antiperspirant composition. Obviously, the skilled worker may select materials that provide the desired application and aesthetic characteristics of the particular form of antiperspirant composition to be produced.

The antiperspirant composition may be formulated as a water-like free flowing liquid or as a thickened solution. Typically the composition will have a viscosity of about 3 cP (0.003 Pas) to about 20,000 cP (20 Pas). Thin solutions will have a viscosity of about 3 cP (0.003 Pas) to about 500 cP (0.5 Pas), while the preferred thickened solutions will have a viscosity of about 1000 cP (1 Pas) to about 20,000 cP (20 Pas), more preferably about 5000 cP (3 Pas) to about 20,000 cP (20 Pas). Viscosity is measured at 21° C. using a Brookfield Model D viscometer with spindle #3.

The viscosity of the solution may be increased or decreased by adjusting the amount and type of thickening agent used. Any thickening agent may be used provided it is compatible with aqueous alcoholic solutions. Particularly suitable thickening agents include the hydroxyalkyl celluloses, such as hydroxyethyl cellulose and hydroxypropyl cellulose. Other thickening agents also may be used such as carboxypolymethylene, carboxy vinyl polymer (e.g., Carbopol), sodium carboxymethyl cellulose, starches, gums, pectins, polyacrylates, etc. If included in the composition, the thickening agent will be present in an amount to provide the desired viscosity, typically about 0.01% to about 5% by weight, more typically about 0.05% to about 2%.

For optimum delivery of the antiperspirant compositions of the present invention, it is preferred to utilize a porous dome applicator comprising a container for holding the antiperspirant composition and a sintered polyethylene porous applicator head affixed to an opening in the container, through which the composition may be delivered to the skin. The present invention may be further illustrated by the following examples in which the parts and percentages are by weight.

EXAMPLE

Antiperspirant solutions were made having the formulations as set out in the table below. Each of these formulations will provide an absolute sweat reduction in excess of 60%.

| Ingredient | Weight Percent | | | |
|---|---|---|---|---|
| | Ex. 1 | Ex. 2 | Ex. 3 | Ex. 4 |
| Water (and) Aluminum Zirconium Tetrachlorohydrex Gly (28–29%) (and) CaCl$_2$ (1.63%)[1] | 50.0 | 76.0 | 60.0 | 76.0 |
| Ethanol | 48.6 | 19.0 | 35.0 | 20.0 |
| Hydroxypropyl cellulose | 0.4 | | | |
| Hydroxyethyl cellulose | | 0.4 | | 0.2 |
| C11–15 Pareth-12 (and) PEG-40 Hydrog. Castor Oil | | 3.0 | | 3.0 |
| Butylene carbonate | | | 3.0 | |
| PPG-5-Ceteth-20 | | | 1.0 | |
| Fragrance | 1.0 | 1.6 | 1.0 | 0.8 |

[1]Antiperspirant salt includes about 3.4% glycine and about 1.8% Ca.

What is claimed is:

1. A liquid aqueous alcoholic antiperspirant solution comprising, by weight, about 15% to about 55% ethanol, about 25% to about 70% water, and about 8% to about 22% (USP) antiperspirant salt dissolved in the solution, wherein said antiperspirant salt comprises a calcium enhanced aluminum-zirconium chlorohydrate, wherein the calcium enhanced aluminum-zirconium chlorohydrate (when measured as a 10% solution) has an HPLC peak 4 to peak 3 area ratio of at least 0.5 with at least 70% of the aluminum contained in said peaks 3 and 4.

2. The antiperspirant solution of claim 1 wherein the calcium enhanced aluminum-zirconium chlorohydrate (when measured as a 10% solution) has an HPLC peak 4 to peak 3 area ratio of at least 0.7 with at least 80% of the aluminum contained in said peaks 3 and 4.

3. The antiperspirant solution of claim 2 wherein the calcium enhanced aluminum-zirconium chlorohydrate comprises a soluble calcium salt in an amount to provide a Ca:Al+Zr weight ratio of about 1:1 to about 1:28 and a water soluble amino and/or hydroxy acid in an amount to provide an acid:Al+Zr weight ratio of about 2:1 to about 1:20.

4. The antiperspirant of claim 2 wherein the calcium enhanced aluminum-zirconium chlorohydrate comprises a soluble calcium salt in an amount to provide a Ca:Al+Zr weight ratio of about 1:2 to about 1:25 and a water soluble amino and/or hydroxy acid in an amount to provide an acid:Al+Zr weight ratio of about 1:1 to about 1:10.

5. The antiperspirant solution of claim 4 wherein said calcium salt is selected from the group consisting of calcium chloride, calcium bromide, calcium nitrate, calcium citrate, calcium format, calcium acetate, calcium gluconate, calcium ascorbate, calcium lactate, calcium glycinate, calcium carbonate, calcium sulfate, calcium hydroxide and mixtures two or more of these.

6. The antiperspirant solution of claim 5 wherein said amino and/or hydroxy acid is selected from the group consisting of glycine, alanine, valine, leucine, isoleucine, β-alanine, serine, cysteine, β-amino-n-butyric acid, γ-amino-n-butyric acid, glycolic acid, lactic acid and mixtures of two or more of these.

7. The antiperspirant solution of claim 6 comprising about 18% to about 50% ethanol and about 30% to about 60% water.

8. The antiperspirant solution of claim 4 wherein said calcium salt comprises calcium chloride and/or calcium glycinate, and wherein said amino and/or hydroxy acid comprises glycine.

9. The antiperspirant solution of claim 8 comprising about 18% to about 50% ethanol and about 30% to about 60% water.

10. The antiperspirant solution of claim 1 or 7 additionally comprising a thickening agent.

11. The antiperspirant solution of claim 10 wherein the thickening agent comprises hydroxyethyl cellulose or oxypropyl cellulose.

12. That antiperspirant solution of claim 1 or 7 having a viscosity of about 3 cP (0.003 Pas) to about 20,000 cP (20 Pas) at 21° C.

13. The antiperspirant solution of claim 10 having a viscosity of about 5000 cP (5 Pas) to about 20,000 cP (20 Pas) at 21° C.

14. The antiperspirant solution of claim 1 or 7 wherein the calcium enhanced aluminum-zirconium chlorohydrate comprises aluminum-zirconium tetrachlorohydrex-gly or aluminum-zirconium octachlorohydrex-gly.

15. The antiperspirant solution of claim 10 wherein the calcium enhanced aluminum-zirconium chlorohydrate comprises aluminum-zirconium tetrachlorohydrex-gly or aluminum-zirconium octachlorohydrex-gly.

16. The antiperspirant solution of claim 1 or 7 contained in a porous dome applicator comprising a container for holding the antiperspirant solution and a sintered polyethylene pore applicator head affixed to an opening in the container, through which the solution may be delivered to the skin.

17. The antiperspirant solution of claim 13 contained in a porous dome applicator comprising a container for holding the antiperspirant solution and a sintered polyethylene porous applicator head affixed to an opening in the container, through which the solution may be delivered to the skin.

18. The antiperspirant solution of claim 1 or 7, optionally including other cosmetic ingredients that are soluble or dispersible therein.

19. The antiperspirant solution of claim 18, wherein said other cosmetic ingredients are selected from a polyhydric alcohol, a surfactant, a fragrance, an encapsulated fragrance, a colorant, a deodorant active agent, an odor-masking agent, an emollient, or a combination of one or more of these ingredients.

* * * * *

UNITED STATES PATENT AND TRADEMARK OFFICE
CERTIFICATE OF CORRECTION

PATENT NO. : 6,942,850 B2
DATED : September 13, 2005
INVENTOR(S) : Craig M. Coe et al.

It is certified that error appears in the above-identified patent and that said Letters Patent is hereby corrected as shown below:

<u>Column 4,</u>
Line 10, after "antiperspirant" insert -- solution --.
Line 42, replace "oxypropyl" with -- hydroxypropyl --.
Line 60, replace "pore" with -- porous --.

Signed and Sealed this

First Day of November, 2005

JON W. DUDAS
*Director of the United States Patent and Trademark Office*